(12) United States Patent
Lee (10) Patent No.: US 11,116,842 B2
(45) Date of Patent: Sep. 14, 2021

(54) METHYLENE BLUE COMPLEX FOR TREATING SKIN DISEASE AND ITS USE THEREOF

(71) Applicant: D. R. NANO Co., Ltd., Seoul (KR)

(72) Inventor: Yong-Deok Lee, Namyangju-si (KR)

(73) Assignee: D. R. NANO CO., LTD., Seoul (KR)

( * ) Notice: Subject to any disclaimer, the term of this patent is extended or adjusted under 35 U.S.C. 154(b) by 27 days.

(21) Appl. No.: 15/696,514

(22) Filed: Sep. 6, 2017

(65) Prior Publication Data
US 2018/0243417 A1 Aug. 30, 2018

(30) Foreign Application Priority Data
Feb. 27, 2017 (KR) .................. 10-2017-0025286

(51) Int. Cl.
*A61K 41/00* (2020.01)
*A61K 31/60* (2006.01)
(Continued)

(52) U.S. Cl.
CPC .......... *A61K 41/008* (2013.01); *A61K 9/1075* (2013.01); *A61K 31/5415* (2013.01); *A61K 31/60* (2013.01); *A61K 41/0057* (2013.01); *A61K 47/542* (2017.08); *A61K 47/545* (2017.08); *A61K 47/6907* (2017.08);
(Continued)

(58) Field of Classification Search
None
See application file for complete search history.

(56) References Cited

U.S. PATENT DOCUMENTS

2002/0128695 A1 9/2002 Harth et al.
2008/0014248 A1 1/2008 Park et al.
(Continued)

OTHER PUBLICATIONS

Patel "Targeted methylene blue-containing polymeric nanoparticle formulations for oral antimicrobial photodynamic therapy", Mater Thesis, Northeastern University, Boston Massachusetts (Year: 2009).*
(Continued)

*Primary Examiner* — Isis A Ghali
(74) *Attorney, Agent, or Firm* — STIP Law Group, LLC (57) ABSTRACT

The present invention relates to complex particles using methylene blue for treating a skin disease caused by *Propionibacterium acnes* or *Staphylococcus aureus* and a composition for treatment including the complex particles. The complex particles in the present invention can be used as a photosensitizer for a photodynamic therapy and complex particles having a micelle form in which hydrophilic methylene blue and two hydrophobic organic acids are combined, and as a result, pore penetration is easy and an occlusion time can be significantly reduced to 30 minutes as compared with conventional phototherapy requiring an occlusion time of 1 hour to 3 hours. Further, in order to reduce side effects of a residual photosensitizer in phototherapy using an existing photosensitizer due to photoreaction and photobleaching of the methylene blue-organic acid complex, a light protection (light blocking or light shielding) time when contact of light needs to be avoided for 24 hours or more after treatment can be significantly reduced to 3 hours, and target treatment for *Propionibacterium acnes, Staphylococcus aureus*, or the like which is a cause of acne is possible.

6 Claims, 7 Drawing Sheets

Methylene Bule (MB, Positively Charged)

Organic acid X (Organic acid 1)
X= DHA, IAA, Tranexamic acid, Sodium salicylate, Ascorbic acid Sodium Oleate (Organic acid 2)

MBX NPs (Charge complex NPs)

(51) Int. Cl.
   *A61P 17/10*      (2006.01)
   *A61K 31/5415*   (2006.01)
   *A61K 47/69*      (2017.01)
   *A61K 47/54*      (2017.01)
   *A61K 9/107*      (2006.01)
   *A61N 5/06*       (2006.01)

(52) U.S. Cl.
   CPC ........... *A61N 5/062* (2013.01); *A61N 5/0616* (2013.01); *A61P 17/10* (2018.01)

(56) References Cited

U.S. PATENT DOCUMENTS

2009/0093470 A1* 4/2009 Loebel ............... A61K 31/5415
                                                              514/224.8
2009/0291944 A1* 11/2009 Ash ........................ A01N 31/02
                                                              514/227.5
2015/0273084 A1* 10/2015 Kim ................... A61K 49/0082
                                                              424/9.6

OTHER PUBLICATIONS

Zolfaghari et al. "In vivo killing of *Staphylococcus aureus* using a light-activated antimicrobial agent", BMC Microbiology, Feb. 2009.*
Desbois et al. "Antibacterial activity of long-chain polyunsaturated fatty acids against propionibacterium acnes ans *Staphylococcus aureus*", Marine Drugs, 4544-4557, Nov. 13, 2013.*
M. Wan et al; Current evidence and applications of photodynamic therapy in dermatology; Clinical, Cosmetic and Investigational Dermatology; May 21, 2014; pp. 145-163; vol. 7; DovePress; Auckland, New Zealand.

* cited by examiner

[FIG. 1]

MBX NPs (Charge complex NPs)

Methylene Blue (MB, Positively Charged)

Organic acid X (Organic acid 1)

X= DHA, IAA, Tranexamic acid,
Sodium salicylate, Ascorbic acid

Sodium Oleate (Organic acid 2)

| | Name | Abs (nm) | FL (nm) | Size (nm) | SOG QY (Ref=Methylene Blue) | Clearance time (with Healite 633) | Viability (%) (S. Aureus) | |
|---|---|---|---|---|---|---|---|---|
| | | | | | | | Photo | Dark |
| 1 | MBD NP (MB+DHA) | 632 | 665 | 106.3 ± 4.27 | 0.14 | 5 min | 24.1 | 25.8 |
| 2 | MBI NP (MB+Oleate) | 638 | 673 | 98.33 ± 8.98 | 0.12 | 7 min | 31.5 | 37.9 |
| 3 | MBT NP (MB+Tranexamic acid) | 649 | 678 | 64.81 ± 7.74 | 0.12 | 5 min | 36.2 | 51.4 |
| 4 | MBS NP (Salicylic acid) | 647 | 683 | 78.9 ± 4.54 | 0.13 | 5 min | 0 | 86.5 |
| 5 | MBA NP (MB+Ascorbic acid) | 639 | 673 | 84.67 ± 6.67 | 0.13 | 3 min | 56.6 | 68.8 |

* SOG QY of PpIX = 0.56

Journal of Photochemistry and Photobiology B. Biology 37 (1997) 131 - 140

METHYLENE BLUE COMPLEX FOR TREATING SKIN DISEASE AND ITS USE THEREOF

CROSS-REFERENCE TO RELATED APPLICATIONS

This application claims the priority of the Korean Patent Applications NO 10-2017-0025286 filed on Feb. 27, 2017, in the Korean intellectual Property Office, the disclosure of which is incorporated herein by reference.

TECHNICAL FIELD

The present invention relates to complex particles for treating a skin disease such as acne caused by acne bacteria, *Staphylococcus aureus*, or the like, containing methylene blue and organic acids and a composition for treating a skin disease such as acne, including the complex particles.

BACKGROUND ART

In general, acne is an inflammation caused by causative bacteria such as *Propionibacterium acnes* (*P. acnes*), *Staphylococcus aureus* (*S. aureus*), or *Acarus folliculorum*, in which while the sebaceous glands in the dermal layer of the skin are accelerated, sebum secretion is increased and the pores are clogged. During puberty, as the sebaceous glands are matured by hormone stimulation of androgen, acne begins, but as adults, the acne is caused by stimulating the sebaceous glands while the sebum is not secreted well by makeup or adrenocortical hormone is increased by stress, lack of sleep, or the like.

A basic concept of a photodynamic therapy (PDT) method is to use a principle in which a photosensitizer exposed to light generates singlet oxygen and other active oxygen species to kill bacteria that cause inflammation. The PDT method is introduced as a method of effectively treating acne by reducing *Propionibacterium acnes* or *Staphylococcus aureus* and decreasing the sebaceous glands abnormally enlarged by active oxygen, vascular occlusion, immunity, and sterilization such as apoptosis for *Propionibacterium acnes* which is a causative bacterium of acne or *Staphylococcus aureus* capable of causing pyogenic inflammation, and currently, operations through the PDT have been performed by many hospitals and clinics.

The PDT method is a treating method in which first, when the photosensitizer is coated on the skin surface, the photosensitizer is selectively absorbed in the sebaceous glands and the pores, and when a laser beam with a specific wavelength is irradiated thereto, the photosensitizer in the sebaceous glands and the pores is activated and singlet oxygen is generated, and as a result, the sebaceous glands are damaged and the *Propionibacterium acnes* in the pores is killed, and simultaneously, a horny layer removal (peeling effect) phenomenon on the skin surface occurs to smoothly secrete the sebum through the peeling effect of removing the keratin which has blocked the pores.

When the PDT is received, inflammatory acne can be rapidly recovered and the recurrence rate of the acne is significantly lowered, and the occurrence of blackhead is reduced due to a decrease in secretion of sebaceous glands to have a pore reduction effect.

In the photosensitizer for effective treatment, characteristics, such as stability in vivo, targeting, minimization of substance toxicity when light is not irradiated, efficient transmission of light from the surface of the body to a diseased site, and high photoreactivity, are required.

As a phototherapy agent which is frequently used at present, 5-aminolevulinic acid (ALA), Methyl-aminolevulinate (MAL), tryptophan, and the like are used, and particularly, the ALA and the MAL are metabolized by a porphyrin-based photosensitizer after intracellular impregnation to have a photodynamic therapy effect by the light with the specific wavelength. As a result, since a metabolic time after administration to the affected site is required, a relatively long occlusion time of about 2 hours or more is required. As a result, the ALA and the MAL have disadvantages that treatment cost is increased, and it is effective for short-term acne treatment, but xeroderma is caused in a long-term application, and in order for a patient to maintain a normal daily life after treatment, it needs a light protection time (light blocking time, light shielding time, and clearance time) of at least 40 hours, the patient should be careful of strong light stimuli. Further, the ALA and the MAL have disadvantages that during photodynamic therapy, singlet oxygen is generated at various places of the skin to cause death of healthy cells in addition to *Propionibacterium acnes* and *Staphylococcus aureus* or damage of sebaceous glands, and thus, effective target treatment is impossible.

Meanwhile, the methylene blue has been studied as various treating materials (Marilyn T Wan, Jennifer Y Lin. Current evidence and applications of photodynamic therapy in dermatology. Clinical, Cosmetic and Investigational Dermatology 7 (1): 145-163), and recently, the methylene blue has been used for PDT for skin diseases using methylene blue. However, the methylene blue is a hydrophilic molecule that is difficult to pass through a cell membrane or a lipid layer of the skin and has low target orientation, and thus, in order to use methylene blue as a photosensitizer for efficient and target-oriented PDT treatment of skin diseases, it is required to convert properties by combining the methylene blue with other hydrophobic particles, and the like.

Throughout this specification of the present invention, several papers and patent documents are referenced and their citations are indicated. The disclosures of the cited papers and patent documents are entirely incorporated to this specification by reference in this specification and the extent of the art to which the present invention pertains and the contents of the present invention will be more clearly described.

PRIOR ART DOCUMENT

Patent Document (Patent Document 1) US2002/0128695A (APPARATUS AND METHOD FOR HIGH ENERGY PHOTODYNAMIC THERAPY OF ACNE VULGARIS AND SEBORRHEA)

(Patent Document 2) US2008/0014248A (PHOTOSENSITIZER CONTAINING INDOLE-3-ALKYLCARBOXYLIC ACID, AND KIT FOR PHOTODYNAMIC THERAPY CONTAINING THE SAME)

Non-Patent Document

Marilyn T Wan, Jennifer Y Lin. Current evidence and applications of photodynamic therapy in dermatology. Clinical, Cosmetic and Investigational Dermatology 7 (1): 145-163

DISCLOSURE

Technical Problem

In order to solve the problems of the porphyrin-based photosensitizer used in the photodynamic therapy, the present invention uses methylene blue which is an alternative photosensitizer. A first object of the present invention is to provide complex particles having a micelle form by combining hydrophilic methylene blue and two kinds of organic acids at an appropriate ratio so as to minimize side effects and photosensitivity after treatment by reducing an occlusion time for generating an effect after administration to an affected site during photodynamic therapy and simultaneously, reducing a light protection time after treatment to more than 0 hour and less than 3 hours and enhance cell permeability by effectively administering the photosensitizer to skin lipids and enable effective photodynamic therapy.

Another object of the present invention is to provide particles formed by combining methylene blue, organic acids, and a surfactant in order to solve a phenomenon in which singlet oxygen is generated anywhere in addition to an onset during photodynamic therapy using methylene blue which is a problem in the related art. The complex particle of the present invention has a micelle form in which methylene blue particles are positioned at the center and a hydrophobic surfactant is positioned at the outside, and the singlet oxygen is generated only at the onset and availability of a photodynamic therapy by using the photosensitizer in the present invention for target treatment is high.

Further, yet another object of the present invention is to provide a composition for treating a skin disease such as acne, including complex nanoparticles containing methylene blue, organic acids, and a surfactant for effective photodynamic therapy for acne treatment. The organic acid can be selected from docosahexaenoic acid (DHA), indole-3-acetic acid (IAA), tranexamic acid, salicylic acid, ascorbic acid, linoleic acid, linolenic acid, oleic acid, deoxycholic acid, folic acid, retinoic acid, cholic acid, glycocholic acid, taurocholic acid, chenodeoxycholic acid, glycochenodeoxycholic acid, taurochenodeoxycholic acid, lithocholic acid, salicyl salicylic acid, acetylsalicylic acid, methyl salicylic acid, and phenylacetic acid. The methylene blue complex particles are used for photodynamic therapy to treat the acne.

Technical Solution

An aspect of the present invention provides methylene blue complex particles configured by methylene blue and two kinds of organic acids.

In a mass ratio of the methylene blue, the organic acid 1, and the organic acid 2 for forming the methylene blue complex particles of the present invention, a mass of the organic acid 1 may be 1 to 5 times greater than the mass of the methylene blue and a mass of the organic acid 2 may be 50 to 500 times greater than the mass of the mixture of the methylene blue and the organic acid 1. The organic acids 1 and 2 may be different organic acids.

As another preferable example of the present invention, in a mass ratio of methylene blue, the organic acids and a surfactant for forming the methylene blue complex particles of the present invention, a mass of the organic acid may be 1 to 5 times greater than the mass of the methylene blue and a mass of the surfactant may be 50 to 500 times greater than the mass of the mixture of the methylene blue and the organic acid.

In phototherapy using the methylene blue complex particles of the present invention, an occlusion time after administration to the affected site is more than 0 and 1 hour or less, preferably, more than 0 and 30 minutes or less, and a light protection time when a patient can maintain a normal daily life after the therapy is more than 0 and 3 hours or less, preferably more than 0 and 1 hour or less, and most preferably more than 0 and 30 minutes or less.

The methylene blue complex particles of the present invention are configured only by the compounds of which the biostability of a composition containing the compounds is proven to be safe through clinical trials and human-derived materials.

As a preferable exemplary embodiment of the present invention, a diameter of the methylene blue complex particle of the present invention may be 50 nm or more and 100 μm or less, preferably 50 nm or more and 200 nm or less.

As a preferable exemplary embodiment of the present invention, the surfactant used in the methylene blue complex particles of the present invention may use an oleic acid.

As a preferable exemplary embodiment of the present invention, the methylene blue complex particles of the present invention may treat acne caused by *Propionibacterium acnes, Staphylococcus aureus*, or the like.

As the organic acids used in the methylene blue nanoparticle of the present invention, docosahexaenoic acid (DHA), indole-3-acetic, acid (IAA), tranexamic acid, salicylic acid, ascorbic acid, linoleic acid, linolenic acid, oleic acid, deoxycholic acid, folic acid, retinoic acid, cholic acid, glycocholic acid, taurocholic acid, chenodeoxycholic acid, glycochenodeoxycholic acid, taurochenodeoxycholic acid, lithocholic acid, salicyl salicylic acid, acetylsalicylic acid, methyl salicylic acid, and phenylacetic acid represented by Chemical Formulas 1 to 22 given below, respectively, and the most preferable organic acids contained in the methylene blue complex particles in the present invention are salicylic acid and oleic acid.

[Chemical Formula 1]

DHA(docosahexaenoic acid)

[Chemical Formula 2]

[AA (Indole-3-acetic acid)

[Chemical Formula 3]

Tranexamic acid

[Chemical Formula 4]

Salicylic acid

[Chemical Formula 5]

Ascorbic acid

[Chemical Formula 6]

Linoleic acid

[Chemical Formula 7]

Linolenic acid

[Chemical Formula 8]

Oleic acid

[Chemical Formula 9]

Deoxycholic acid

[Chemical Formula 10]

Folic acid

[Chemical Formula 11]

Retinoic acid

[Chemical Formula 12]

Cholic acid

[Chemical Formula 13]

Glycocholic acid

[Chemical Formula 14]

Taurocholic acid

[Chemical Formula 15]

Chenodeoxycholic acid

[Chemical Formula 16]

Glycochenodeoxycholic acid

[Chemical Formula 17]

Taurochenodeoxycholic acid

[Chemical Formula 18]

Lithocholic acid

[Chemical Formula 19]

Salicylsalicylic acid

[Chemical Formula 20]

Acetylsalicylic acid

[Chemical Formula 21]

Methyl salicylic acid

[Chemical Formula 22]

Phenylacetic acid

The methylene blue is a dye coupled with a phenothiazine group and when exposed to light the phenothiazine group reacts to generate a viricidal effect. The viricidal effect has been known since the 1940s and the methylene blue has been used for sterilization treatment of *Staphylococcus aureus* by using the characteristic.

The methylene blue is a positively charged dye and the methylene blue itself is very difficult to be introduced into cells, but the methylene blue complex particle of the present invention is formed by containing methylene blue with a positively charged property and two kinds of fatty acid-based organic acids with a negatively charged property having a hydrophobic property. As the result, the complex particle in the present invention having an amphiphilic property in which a methylene blue particle is positioned at the center and the two kinds of organic acids is configured in a micelle form, and thus, in a hydrophilic solvent, the hydrophobic part of the molecule is gathered at the center to form a nuclei and the hydrophilic part forms an outer portion contacting water. As a result, the methylene blue complex particle of the present invention is stabilized and dissolved in a water-soluble solvent because the hydrophobic part is positioned at the inner side of the micelle. Accordingly, since the hydrophobic part is positioned at the outer portion at the moment of contact the skin made of lipid, the complex particle has a hydrophobic property to exhibit high permeability to the skin lipid.

In an exemplary embodiment, the methylene blue complex particle may be prepared by a method of mixing methylene blue and an organic acid to form a methylene blue-organic acid mixture, lyophilizing the mixture to form a complex, and then mixing the mixture obtained above with another organic acid, but the present invention is not limited thereto.

Advantageous Effects

The nanoparticles used as a photosensitizer for photodynamic therapy of the present invention are complex particles having a micelle form configured by hydrophilic methylene blue and hydrophobic organic acids, and as a result, pore penetration is easy and an occlusion time can be significantly reduced to 1 hour or less as compared with conventional phototherapy requiring a metabolism time of 2 hours to 3 hours. Further, due to photoreaction and photobleaching of the methylene blue-organic acid complex, a light protection, light blocking, or light shielding time can be significantly reduced to 3 hours or less from about 40 hours required in the case of using a traditional photosensitizer in order to reduce side effects of a residual photosensitizer in existing phototherapy in the prior arts, and the present invention can be possibly used to administrate a target treatment for *Propionibacterium acnes, Staphylococcus aureus*, or the like which is a cause of acne.

DESCRIPTION OF DRAWINGS

FIG. 6A and FIG. 6B illustrate evaluation of photo-toxicity of complex particle formed by using methylene blue and salicylic acid in Example 5, in which

MODES OF THE INVENTION

Hereinafter, the present invention will be described in more detail through Examples. These Examples are just to describe the present invention in more detail and it is apparent to those skilled in the art that the scope of the present invention is not limited to these Examples.

EXAMPLES

Example 1: Preparation of Hydrophobic Complex of Photosensitizer (Methylene Blue) and Organic Acids (1) Hydrophobicization of Methylene Blue/DHA by Electrostatic Force 20 mg of methylene blue (MB, purchased from Aldrich) and 20 mg of DHA (D, purchased from Aldrich) were heated in 50 mL of tetrahydrofuran (THF, purchased from Daejeong Chemical) for 1 to 5 minutes at 60 to 90° C. and the MB was dissolved. The mixture in which the MB was dissolved was filtered by using a hydrophobic injection filter (0.2 μm), and the obtained filtrate was dried. The MB complex dissolved in the organic layer was extracted by using chloroform and water, purified and lyophilized to obtain an MBD (a complex of the MB and the DHA).

(2) Hydrophobicization of Methylene Blue/IAA by Electrostatic Force 20 mg of methylene blue (MB, purchased from Aldrich) and 20 mg of indole-3-acetic acid (I, purchased from Aldrich) were heated in 50 mL of tetrahydrofuran (THF, purchased from Daejeong Chemical) for 1 to 5 minutes at 60 to 90° C. and the MB was dissolved. The mixture in which the MB was dissolved was filtered by using a hydrophobic injection filter (0.2 μm), and the obtained filtrate was dried. The MB complex dissolved in the organic layer was extracted by using chloroform and water, purified and lyophilized to obtain a MBI (a complex of the MB and the IAA).

(3) Hydrophobicization of Methylene Blue/Tranexamic Acid by Electrostatic Force 20 mg of methylene blue (MB, purchased from Aldrich) and 20 mg of tranexamic acid (T, purchased from Aldrich) were heated in 50 mL of tetrahydrofuran (THF, purchased from Daejeong Chemical) for 1 to 5 minutes at 60 to 90° C. and the MB was dissolved. The mixture in which the MB was dissolved was filtered by using a hydrophobic injection filter (0.2 μm), and the obtained filtrate was dried. The MB complex dissolved in the organic layer was extracted by using chloroform and water, purified and lyophilized to obtain a MBT (a complex of the MB and the tranexamic acid).

(4) Hydrophobicization of Methylene Blue/Salicylic Acid Salt by Electrostatic Force 20 mg of methylene blue (MB, purchased from Aldrich) and 20 mg of salicylic acid salt (S, purchased from Aldrich) were heated in 50 mL of tetrahydrofuran (THF, purchased from Daejeong Chemical) for 1 to 5 minutes at 60 to 90° C. and the MB was dissolved. The mixture in which the MB was dissolved was filtered by using a hydrophobic injection filter (0.2 μm), and the obtained filtrate was dried. The MB complex dissolved in the organic layer was extracted by using chloroform and water, purified and lyophilized to obtain a MBS (a complex of the MB and the salicylic acid).

(5) Hydrophobicization of Methylene Blue/Ascorbic Acid by Electrostatic Force 20 mg of methylene blue (MB, purchased from Aldrich) and 20 mg of ascorbic acid (A, purchased from Aldrich) were heated in 50 mL of tetrahydrofuran (THF, purchased from Daejeong Chemical) for 1 to 5 minutes at 60 to 90° C. and the MB was dissolved. The mixture in which the MB was dissolved was filtered by using a hydrophobic injection filter (0.2 μm), and the obtained filtrate was dried. The MB complex dissolved in the organic layer was extracted by using chloroform and water, purified and lyophilized to obtain a MBA (a complex of the MB and the ascorbic acid).

Example 2: Formation of Self-Assembled Complex Particle Using Complex of Photosensitizer (Methylene Blue) and Organic Acid Hydrophobicized in Aqueous Environment (1) Preparation of Nanoparticles Containing MBD and Amphiphilic Material and Evaluation Thereof 0.2 mg of the MBD obtained in the Example 1 (1) was sufficiently dispersed by using 2 mL of an aqueous solution in which 20 mg of oleate (purchased from Aldrich) was dissolved to prepare complex particles MBD NPs.

Figure 1:
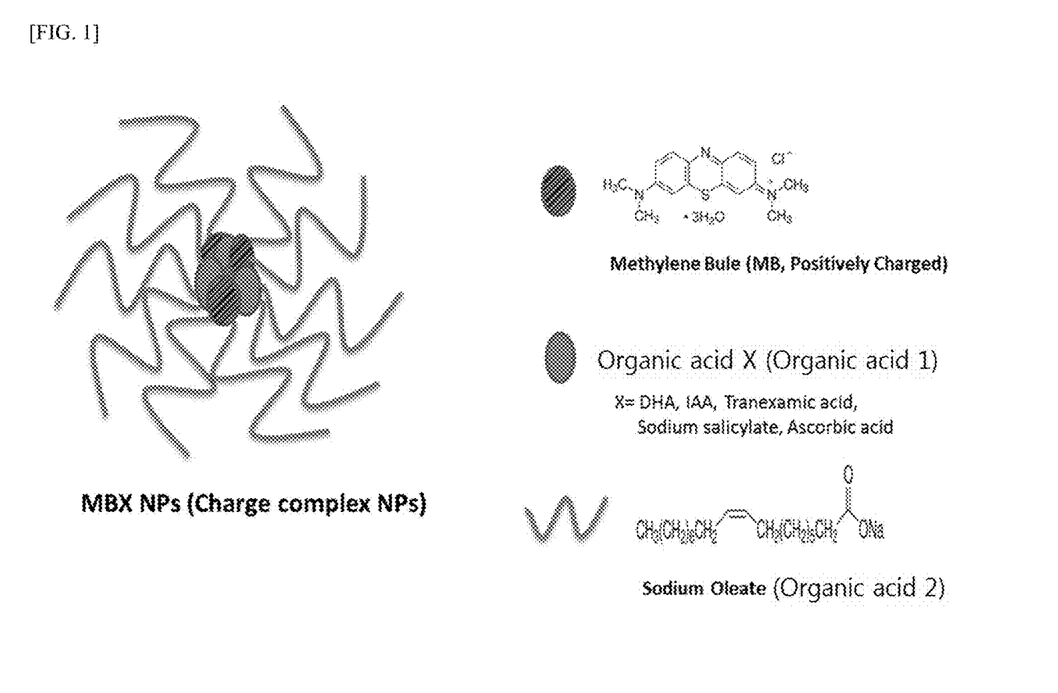
FIG. 1 is a schematic diagram of a complex particle composed of methylene blue-salicylic acid-oleic acid of the present invention.
Figure 2:
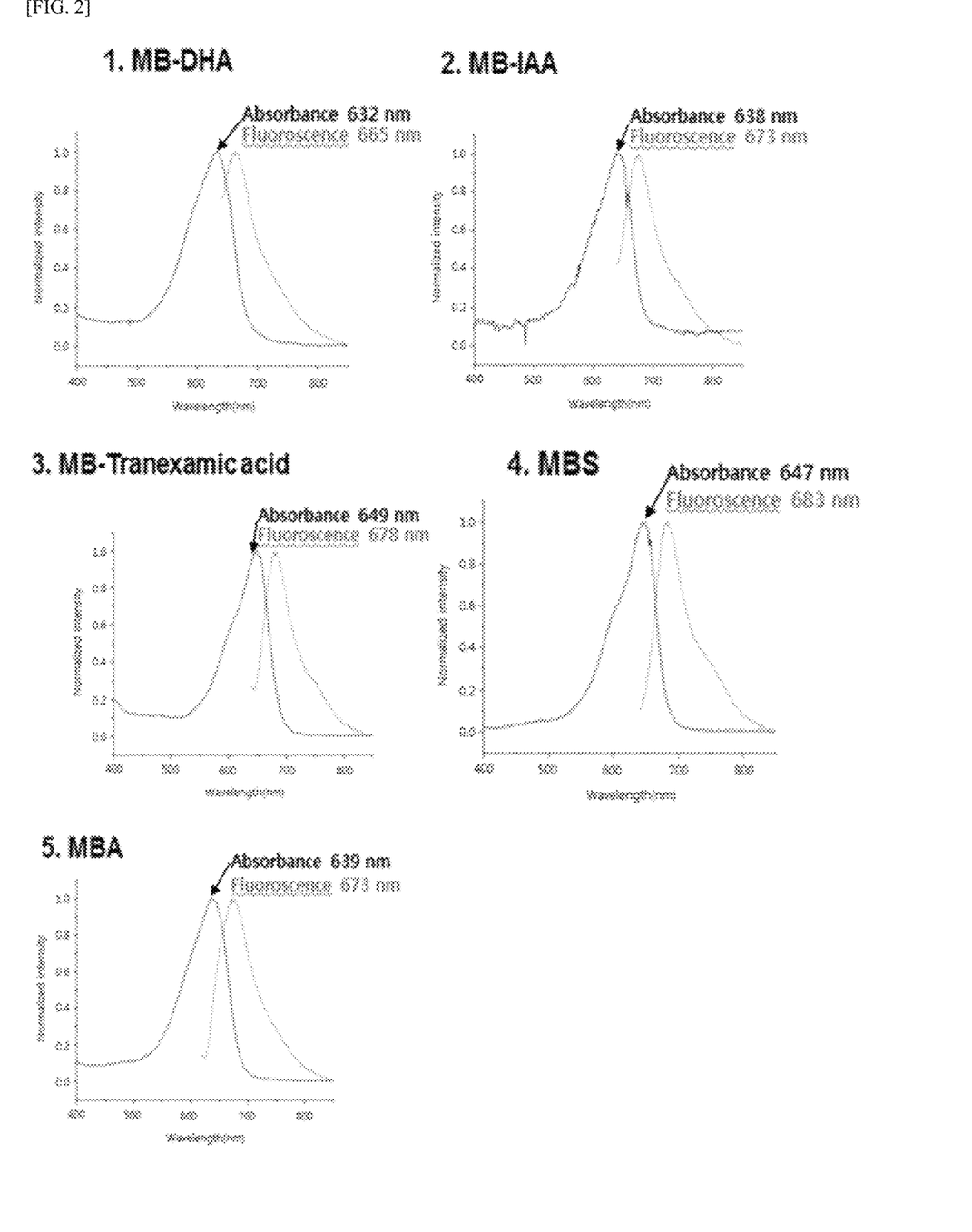
FIG. 2 is a graph illustrated by measuring absorbance and fluorescence intensity when micelle-type complex particles composed of methylene blue and organic acids are dispersed in water.

From FIG. 2 which is a graph illustrated by measuring absorbance and fluorescence of a MB (MB Sol.) dissolved in water and the complex particles MBD NPs dispersed in the water, it was confirmed that an absorption wavelength and a fluorescence wavelength of the MB dissolved in the water moved to a short wavelength region by forming the complex particles.

Figure 3A:
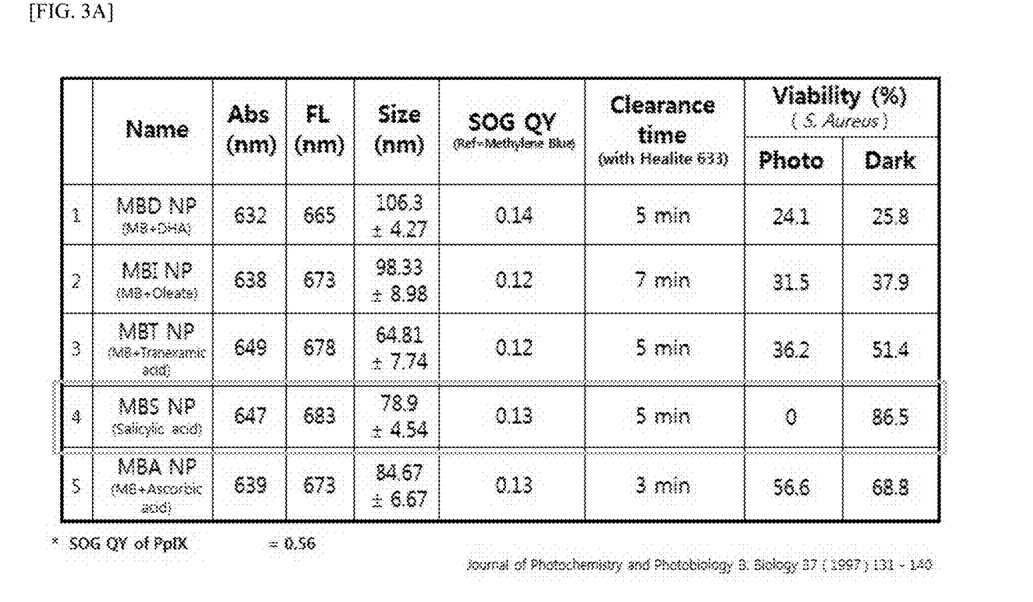
FIGS. 3A and 3B are a table and a distribution diagram illustrated by measuring a size of the complex particle by using a Zetasiser nano ZS and a transmission electron microscope in nanoparticles prepared in Example 1, respectively.
Figure 3B:
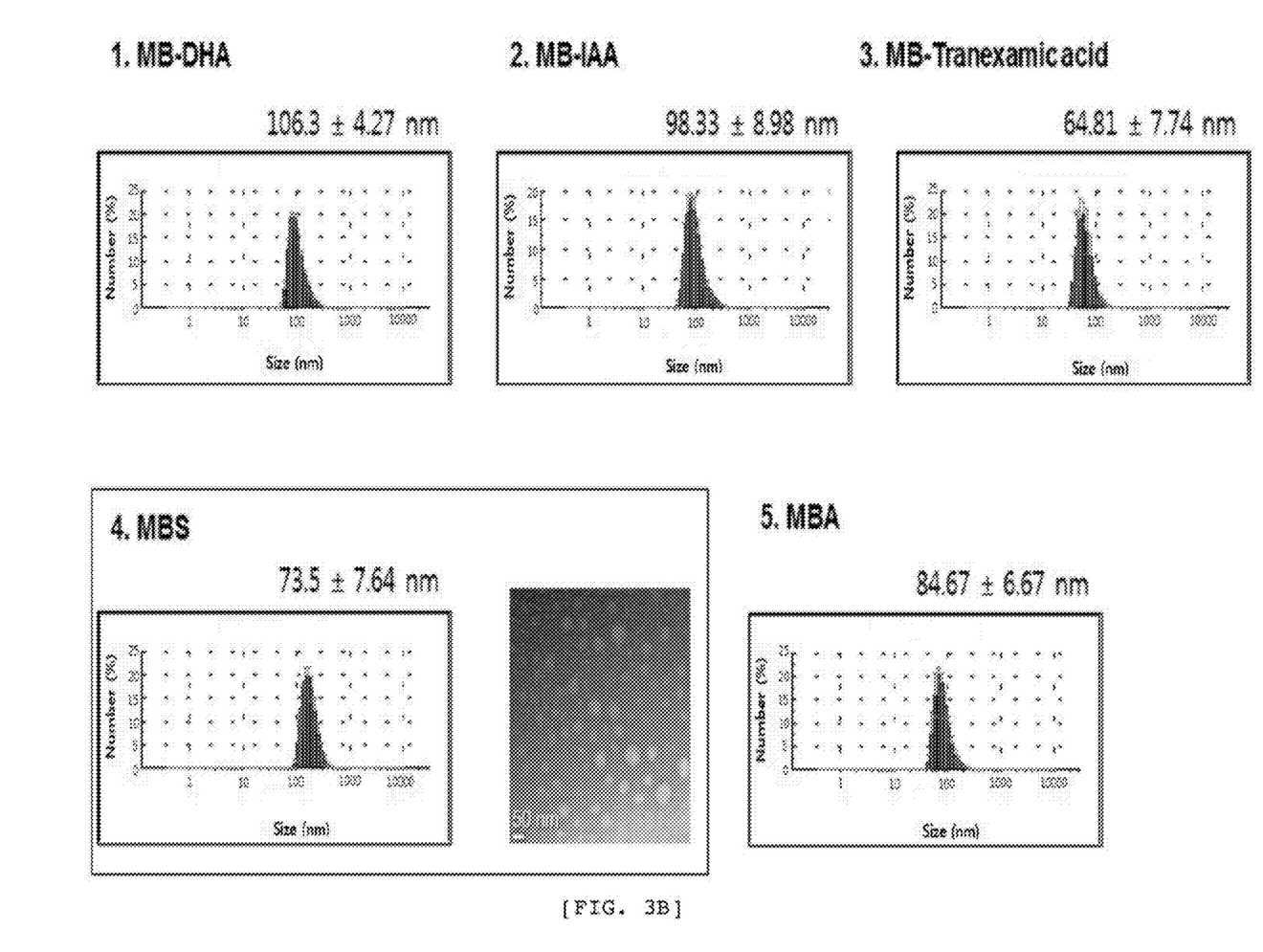

Further, the size and the shape of the complex particle were measured by using a Zetasiser nano ZS (Malvern Instruments, UK) and observed by a transmission electron microscope (TEM, Tecnai) and then illustrated in FIGS. 3A and 3B, respectively. From FIGS. 3A and 3B, it was confirmed that the complex particles were spherical particles having a diameter of 50 to 200 nm.

(2) Preparation of Complex Particles Containing MBI and Amphiphilic Material and Evaluation Thereof 0.2 mg of the MBI obtained in the Example 1 (2) was sufficiently dispersed by using 2 mL of an aqueous solution in which 20 mg of oleate (purchased from Aldrich) was dissolved to prepare complex particles MBD NPs.

From FIG. 2 which is a graph illustrated by measuring absorbance and fluorescence of a MB (MB Sol.) dissolved in water and the complex particles MBI NPs dispersed in the water, it was confirmed that an absorption wavelength and a fluorescence wavelength of the MB dissolved in the water moved to a short wavelength region by forming the complex particles.

Further, the size and the shape of the complex particle were measured by using a Zetasiser nano ZS (Malvern Instruments, UK) and observed by a transmission electron microscope (TEM, Tecnai) and then illustrated in FIGS. 3A and 3B, respectively. From FIGS. 3A and 3B, it was confirmed that the complex particles were spherical particles having a diameter of 50 to 200 nm.

(3) Preparation of Complex Particles Containing MBT and Amphiphilic Material and Evaluation Thereof 0.2 mg of the MBT obtained in the Example 1 (3) was sufficiently dispersed by using 2 mL of an aqueous solution in which 20 mg of oleate (purchased from Aldrich) to prepare complex particles MBT NPs.

From FIG. 2 which is a graph illustrated by measuring absorbance and fluorescence of a MB (MB Sol.) dissolved in water and the complex particles MBT NPs dispersed in the water, it was confirmed that an absorption wavelength and a fluorescence wavelength of the MB dissolved in the water moved to a short wavelength region by forming the complex particles.

Further, the size and the shape of the complex particle were measured by using a Zetasiser nano ZS (Malvern Instruments, UK) and observed by a transmission electron microscope (TEM, Tecnai) and then illustrated in FIGS. 3A and 3B, respectively. From FIGS. 3A and 3B, it was confirmed that the complex particles were spherical particles having a diameter of 50 to 200 nm.

(4) Preparation of Complex Particles Containing MBS and Amphiphilic Material and Evaluation Thereof 0.2 mg of the MBS obtained in the Example 1 (4) was sufficiently dispersed by using 2 mL of an aqueous solution in which 20 mg of oleate (purchased from Aldrich) to prepare complex particles MBS NPs.

From FIG. 2 which is a graph illustrated by measuring absorbance and fluorescence of a MB (MB Sol.) dissolved in water and the complex particles MBS NPs dispersed in the water, it was confirmed that an absorption wavelength and a fluorescence wavelength of the MB dissolved in the water moved to a short wavelength region by forming the complex particles.

Further, the size and the shape of the complex particle were measured by using a Zetasiser nano ZS (Malvern Instruments, UK) and observed by a transmission electron microscope (TEM, Tecnai) and then illustrated in FIGS. 3A and 3B, respectively. From FIGS. 3A and 3B, it was confirmed that the complex particles were spherical particles having a diameter of 50 to 200 nm.

(5) Preparation of Complex Particles Containing MBA and Amphiphilic Material and Evaluation Thereof 0.2 mg of the MBA obtained in the Example 1 (5) was sufficiently dispersed by using 2 mL of an aqueous solution in which 20 mg of oleate (purchased from Aldrich) to prepare complex particles MBA NPs.

From FIG. 2 which is a graph illustrated by measuring absorbance and fluorescence of a MB (MB Sol.) dissolved in water and the complex particles MBA NPs dispersed in the water, it was confirmed that an absorption wavelength and a fluorescence wavelength of the MB dissolved in the water moved to a short wavelength region by forming the complex particles.

Further, the size and the shape of the complex particle were measured by using a Zetasiser nano ZS (Malvern Instruments, UK) and observed by a transmission electron microscope (TEM, Tecnai) and then illustrated in FIGS. 3A and 3B, respectively. From FIGS. 3A and 3B, it was confirmed that the complex particles were spherical particles having a diameter of 50 to 200 nm.

In the Example 1, electrostatic neutralization with the MB and hydrophobicization by the organic acid were performed, and in the Example 2 using them, the MB can be efficiently encapsulated in oleic acid which was fatty acid in an aqueous environment. In the aqueous environment, the complex particles in which the MB was encapsulated in the amphiphilic material had excellent stability to maintain the particle state and the stability was confirmed through the size and the shape.

Example 3: Evaluation of Productivity of Singlet Oxygen of Self-Assembled Complex Particles Containing Methylene Blue as Photosensitizer in Aqueous Environment In order to use the MBS NPs dispersed in the water as a photosensitizer for photodynamic therapy, productivity of singlet oxygen of nanoparticles according to irradiation of a light source was confirmed by comparing with the MB (MB Sol.). The used light source was use a light source (Healite II 633, Lutronics, Co., Ltd.) having a wavelength of 633 nm, in which the MB was known to generate the singlet oxygen.

A generated amount of singlet oxygen may be measured by a chemical method using N,N-dimethyl-4-nitrosoaniline (purchased from Aldrich) which was coupled with the singlet oxygen to lose a unique OD max value.

Figure 4:
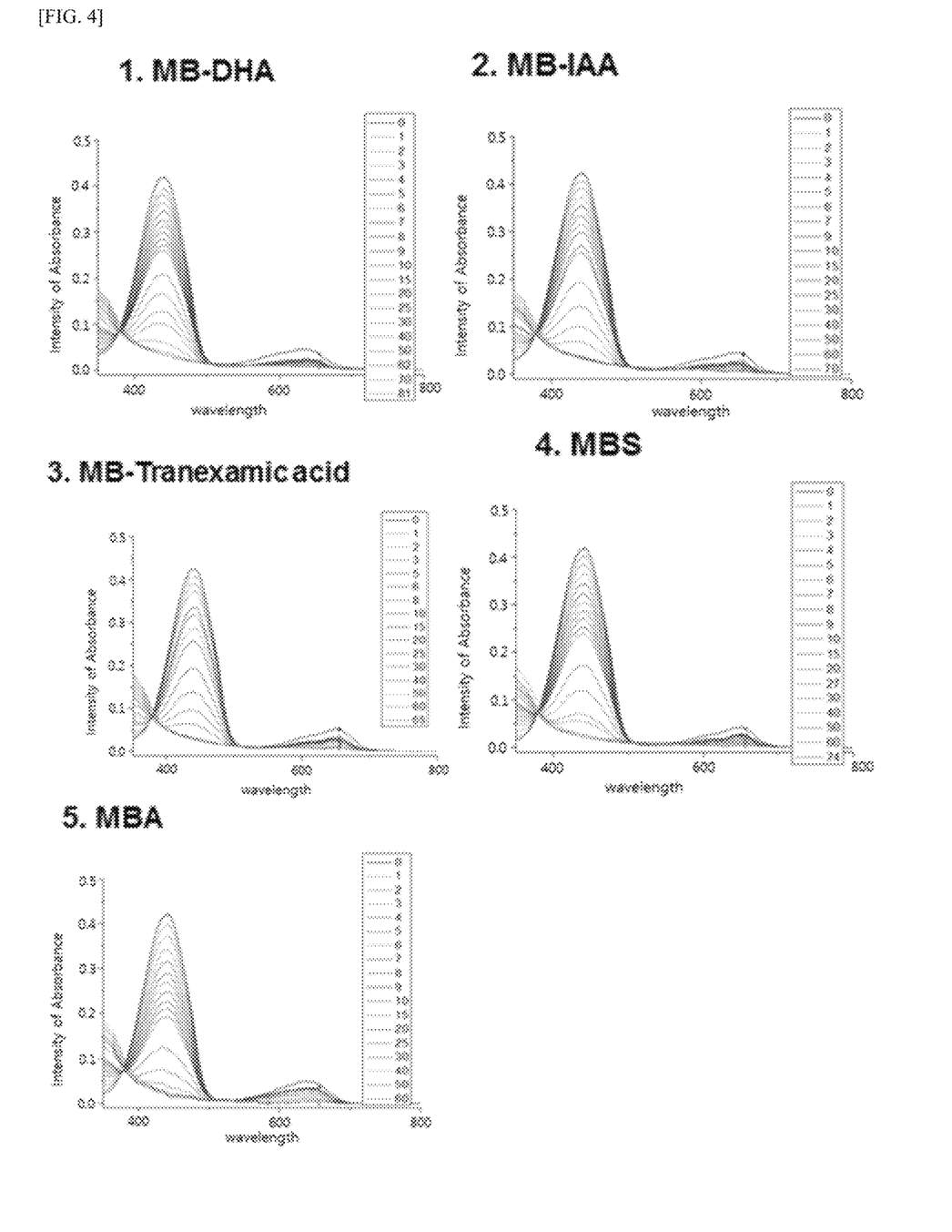
FIG. 4 is a graph illustrating productivity of singlet oxygen when complex particles MBX NPs formed of methylene blue and organic acids of the present invention in which the methylene blue is encapsulated in the complex particle is compared with a methylene blue solution MB Sol. in which the same amount of methylene blue is dissolved in water.

FIG. 4 illustrates the result and confirmed productivity of the singlet oxygen which had no difference when the MBD, MBA, MBT, MBS, and MBA NPs in which the MB was encapsulated in the complex particle were compared with the MB Sol. in which the same amount of MB was dissolved in the water.

Example 4: Evaluation of Photo-Toxicity and Dark-Toxicity for *Staphylococcus Aureus* of Self-Assembled Complex Particles Containing Methylene Blue as Photosensitizer in Aqueous Environment (1) Evaluation of Photo-Toxicity Using *Staphylococcus Aureus*

① Evaluation of Photo-Toxicity of MBD NPs

In order to evaluate photo-toxicity to bacteria of the complex particles MBD NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of nanoparticles per concentration was added (final concentration of 40.4 mg/mL, 20.2 mg/mL, 8.08 mg/mL, 4.04 mg/mL, and 0 mg/mL). For evaluation of photo-toxicity after 10 minutes, light (intensity 4) was irradiated for 10 minutes by using a Healite II 633 (purchased from Lutronics. Co., Ltd.). The bacteria per concentration after light irradiation were diluted to $1\times10^{-6}$ and 1 mL was inoculated in a perifilm (purchased from 3M) and cultured in an incubator (37° C.) for 24 hours, and then the bacterial count was measured.

As a control experiment, an MB aqueous solution corresponding to each concentration of the complex particles was prepared and the bacterial count was measured through the same process as the Example 4 (1) ①.

Further, in order to confirm bacterial toxicity of only the complex particles except for the light source, evaluation of dark-toxicity was performed and illustrated in the Example 4 (2).

② Evaluation of Photo-Toxicity of MBI NPs

In order to evaluate photo-toxicity to bacteria of the complex particles MBI NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of nanoparticles per concentration was added (final concentration of 40.4 mg/mL, 20.2 mg/mL, 8.08 mg/mL, 4.04 mg/mL, and 0 mg/mL). For evaluation of photo-toxicity after 10 minutes, light (intensity 4) was irradiated for 10 minutes by using a Healite II 633 (purchased from Lutronics. Co., Ltd.). The bacteria per concentration after light irradiation were diluted to $1\times10^{-6}$ and 1 mL was inoculated in a perifilm (purchased from 3M) and cultured in an incubator (37° C.) for 24 hours, and then the bacterial count was measured.

As a control experiment, an MB aqueous solution corresponding to each concentration of the complex particles was prepared and the bacterial count was measured through the same process as the Example 4 (1) ②.

Further, in order to confirm bacterial toxicity of only the complex particles except for the light source, evaluation of dark-toxicity was performed and illustrated in the Example 4 (2).

③ Evaluation of Photo-Toxicity of MBT NPs

In order to evaluate photo-toxicity to bacteria of the complex particles MBT NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of complex particles per concentration was added (final concentration of 40.4 mg/mL, 20.2 mg/mL, 8.08 mg/mL, 4.04 mg/mL, and 0 mg/mL). For evaluation of photo-toxicity after 10 minutes, light (intensity 4) was irradiated for 10 minutes by using a Healite II 633 (purchased from Lutronics. Co., Ltd.). The bacteria per concentration after light irradiation were diluted to $1\times10^{-6}$ and 1 mL was inoculated in a perifilm (purchased from 3M) and cultured in an incubator (37° C.) for 24 hours, and then the bacterial count was measured.

As a control experiment, an MB aqueous solution corresponding to each concentration of the complex particles was prepared and the bacterial count was measured through the same process as the Example 4 (1) ③.

Further, in order to confirm bacterial toxicity of only the complex particles except for the light source, evaluation of dark-toxicity was performed and illustrated in the Example 4 (2).

④ Evaluation of Photo-Toxicity of MBS NPs

In order to evaluate photo-toxicity to bacteria of the complex particles MBS NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of complex particles per concentration was added (final concentration of 40.4 mg/mL, 20.2 mg/mL, 4.04 mg/mL, and 0 mg/mL). For evaluation of photo-toxicity after 10 minutes, light (intensity 4) was irradiated for 10 minutes by using a Healite II 633 (purchased from Lutronics. Co., Ltd.). The bacteria per concentration after light irradiation were diluted to $1\times10^{-6}$ and 1 mL was inoculated in a perifilm (purchased from 3M) and cultured in an incubator (37° C.) for 24 hours, and then the bacterial count was measured.

As a control experiment, an MB aqueous solution corresponding to each concentration of the complex particles was prepared and the bacterial count was measured through the same process as the Example 4 (1) ④.

Further, in order to confirm bacterial toxicity of only the complex particles except for the light source, evaluation of dark-toxicity was performed and illustrated in the Example 4 (2).

⑤ Evaluation of Photo-Toxicity of MBA NPs

In order to evaluate photo-toxicity to bacteria of the complex particles MBA NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of complex particles per concentration was added (final concentration of 40.4 mg/mL, 20.2 mg/mL, 8.08 mg/mL, 4.04 mg/mL, and 0 mg/mL). For evaluation of photo-toxicity after 10 minutes, light (intensity 4) was irradiated for 10 minutes by using a Healite II 633 (purchased from Lutronics. Co., Ltd.). The bacteria per concentration after light irradiation were diluted to $1\times10^{-6}$ and 1 mL was inoculated in a perifilm (purchased from 3M) and cultured in an incubator (37° C.) for 24 hours, and then the bacterial count was measured.

As a control experiment, an MB aqueous solution corresponding to each concentration of the complex particles was prepared and the bacterial count was measured through the same process as the Example 4 (1) ⑤.

Further, in order to confirm bacterial toxicity of only the complex particles except for the light source, evaluation of dark-toxicity was performed and illustrated in the Example 4 (2).

(2) Evaluation of Dark-Toxicity Using *Staphylococcus Aureus*

① Evaluation of Dark-Toxicity of MBD NPs

In order to evaluate dark-toxicity to bacteria of the complex particles MBD NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of complex particles per concentration was added (final concentration of 40.4 mg/mL, 20.2 mg/mL, 8.08 mg/mL, 4.04 mg/mL, and 0 mg/mL). The bacteria per concentration were diluted to $1\times10^{-6}$ and 1 mL was inoculated in a perifilm (purchased from 3M) and cultured in an incubator (37° C.) for 24 hours, and then the bacterial count was measured. As a control experiment, an MB aqueous solution corresponding to each concentration of the nanoparticles was prepared and the bacterial count was measured through the same process as the Example 4 (2) ①. All of the processes of the Example 4 (2) ① were performed in a dark room where the light was blocked.

② Evaluation of Dark-Toxicity of MBI NPs

In order to evaluate dark-toxicity to bacteria of the nanoparticles MBI NPs prepared through the Example 1 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of nanoparticles per concentration was added (final concentration of 40.4 mg/mL, 20.2 mg/mL, 8.08 mg/mL, 4.04 mg/mL, and 0 mg/mL). The bacteria per concentration were diluted to $1\times10^{-6}$ and 1 mL was inoculated in a perifilm (purchased from 3M) and cultured in an incubator (37° C.) for 24 hours, and then the bacterial count was measured. As a control experiment, an MB aqueous solution corresponding to each concentration of the complex particles was prepared and the bacterial count was measured through the same process as the Example 4 (2) ②. All of the processes of the Example 4 (2) ② were performed in a dark room where the light was blocked.

③ Evaluation of Dark-Toxicity of MBT NPs

In order to evaluate dark-toxicity to bacteria of the complex particles MBT NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of complex particles per concentration was added (final concentration of 40.4 mg/mL, 20.2 mg/mL, 8.08 mg/mL, 4.04 mg/mL, and 0 mg/mL). The bacteria per concentration were diluted to $1\times10^{-6}$ and 1 mL was inoculated in a perifilm (purchased from 3M) and cultured in an incubator (37° C.) for 24 hours, and then the bacterial count was measured. As a control experiment, an MB aqueous solution corresponding to each concentration of the complex particles was prepared and the bacterial count was measured through the same process as the Example 4 (2) ③. All of the processes of the Example 4 (2) ③ were performed in a dark room where the light was blocked.

④ Evaluation of Dark-Toxicity of MBS NPs

In order to evaluate dark-toxicity to bacteria of the complex particles MBS NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of complex particles per concentration was added (final concentration of 40.4 mg/mL, 20.2 mg/mL, 4.04 mg/mL, and 0 mg/mL). The bacteria per concentration were diluted to $1\times10^{-6}$ and 1 mL was inoculated in a perifilm (purchased from 3M) and cultured in an incubator (37° C.) for 24 hours, and then the bacterial count was measured. As a control experiment, an MB aqueous solution corresponding to each concentration of the complex particles was prepared and the bacterial count was measured through the same process as the Example 4 (2) ④. All of the processes of the Example 4 (2) ④ were performed in a dark room where the light was blocked.

⑤ Evaluation of Dark-Toxicity of MBA NPs

In order to evaluate dark-toxicity to bacteria of the complex particles MBA NPs prepared through the Examples 1 and 2 depending on a concentration, 1 mL of a culture medium (LB medium) in which $1\times10^6$/mL of *Staphylococcus aureus* (*S. aureus*) was dispersed was added in each well of a culture dish (12 well-plate) and then 0.5 mL of complex particles per concentration was added (final concentration of 40.4 mg/mL, 20.2 mg/mL, 8.08 mg/mL, 4.04 mg/mL, and 0 mg/mL). The bacteria per concentration were diluted to $1\times10^{-6}$ and 1 mL was inoculated in a perifilm (purchased from 3M) and cultured in an incubator (37° C.) for 24 hours, and then the bacterial count was measured. As a control experiment, an MB aqueous solution corresponding to each concentration of the nanoparticles was prepared and the bacterial count was measured through the same process as the Example 4 (2) ⑤. All of the processes of the Example 4 (2) ⑤ were performed in a dark room where the light was blocked.

Figure 5:
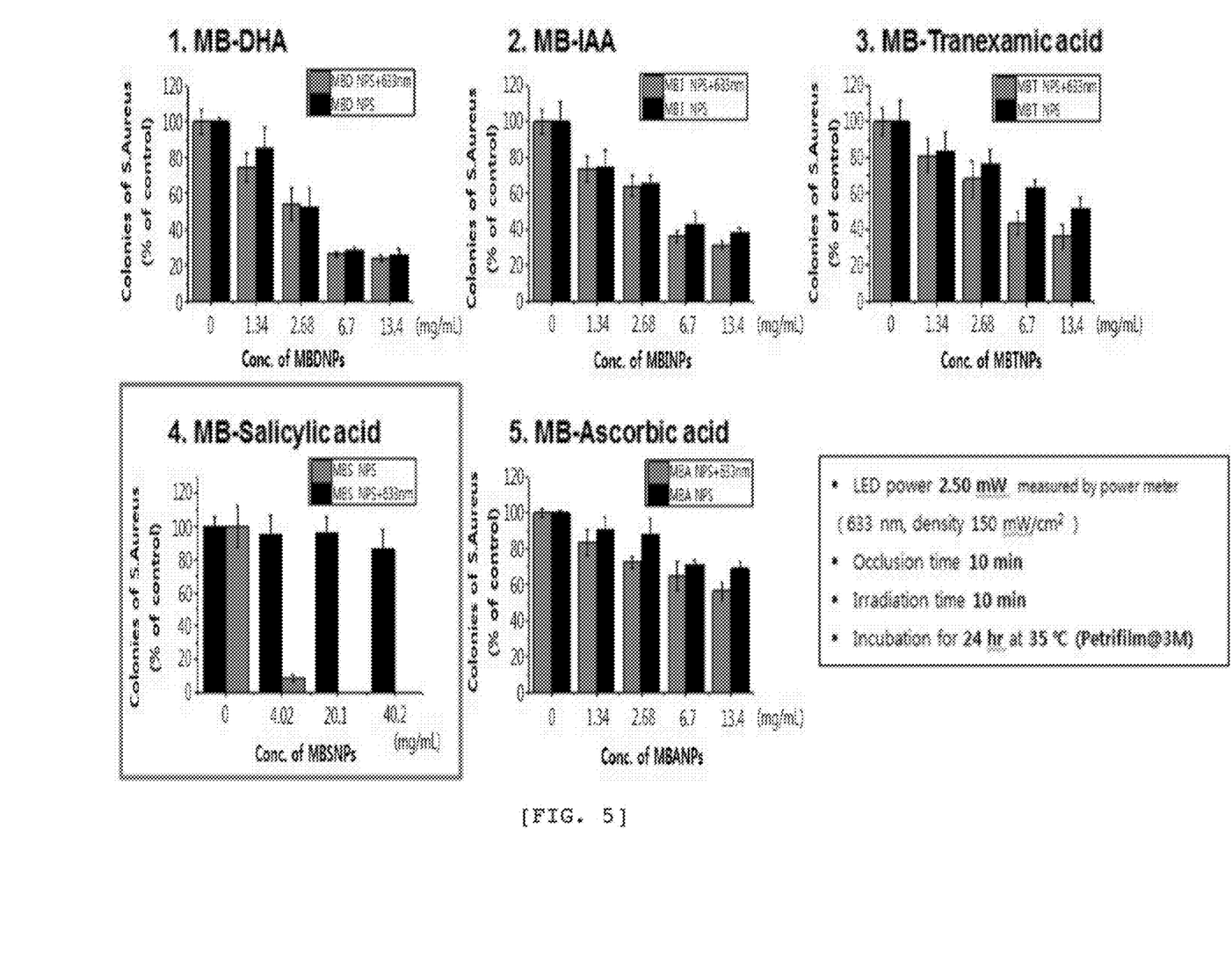
FIG. 5 is a graph illustrating evaluation of photo-toxicity and dark-toxicity in Example 3.

The evaluation of (1) photo-toxicity and (2) dark-toxicity of the Example 4 was illustrated in FIG. 5.

Figure 6A:
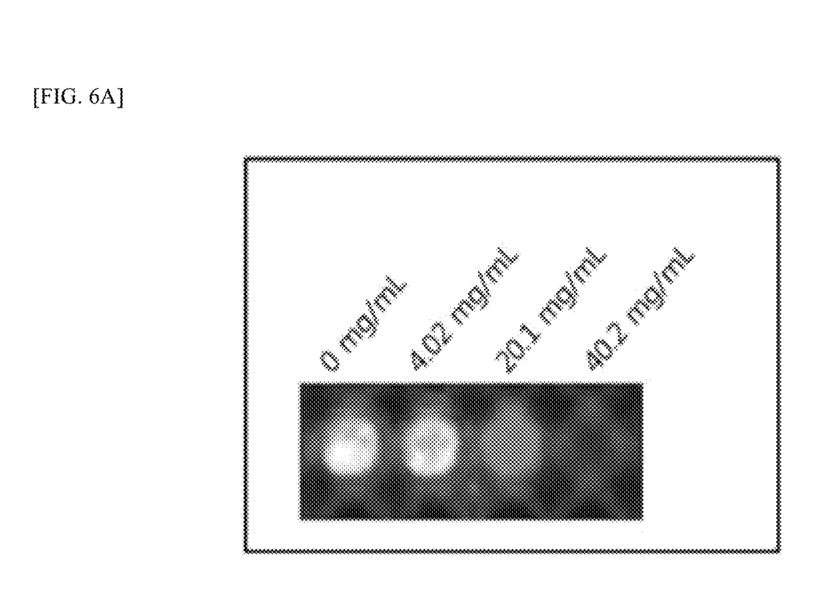
FIG. 6A illustrates an image of *Propionibacterium acnes* (*P. Acnes*)
Figure 6B:
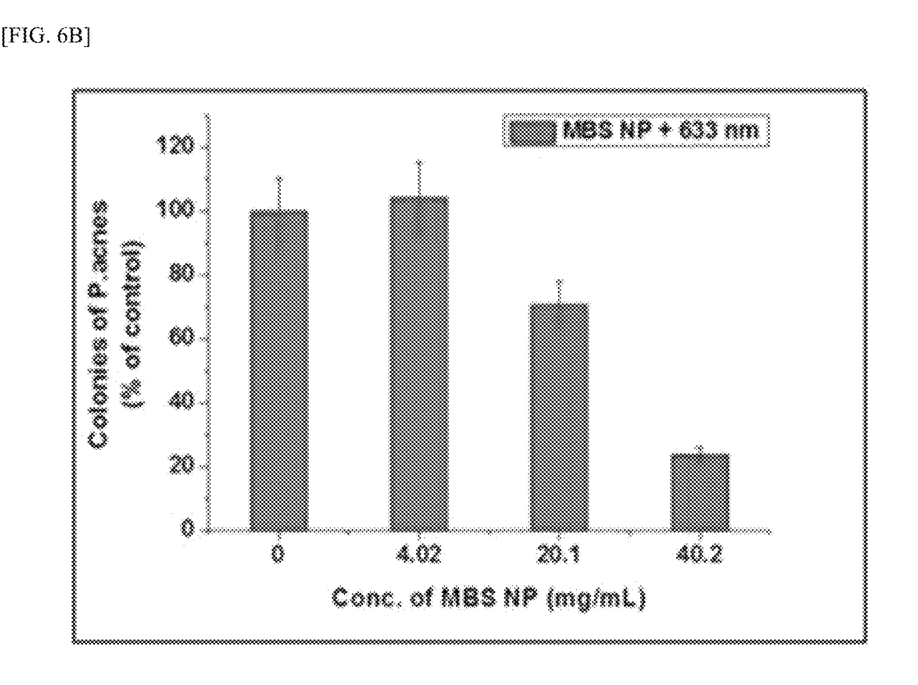
FIG. 6B illustrates evaluation of photo-toxicity for *P. Acnes*.

Example 5: Evaluation of Photo-Toxicity for *Propionibacterium Acnes* (*P. Acnes*) of Self-Assembled Complex Particles Containing Methylene Blue and Salicylic Acid as Photosensitizer in Aqueous Environment In order to evaluate photo-toxicity to *Propionibacterium acnes* of MBS NPs having the highest productivity of singlet oxygen selected from complex particles prepared through the Examples 1 and 2 depending on a concentration in the same light irradiation, 1 mL of a culture medium (LB medium) in which $1\times10^6$/mL of *Propionibacterium acnes* (*P. Acnes*) was dispersed was added in each well of a culture dish (12 well-plate) and then 0.5 mL of complex particles per concentration was added (final concentration of 40.4 mg/mL, 20.2 mg/mL, 4.04 mg/mL, and 0 mg/mL). For evaluation of photo-toxicity after 10 minutes, light (intensity 4) was irradiated for 10 minutes by using a Healite II 633 (purchased from Lutronics. Co., Ltd.). The bacteria per concentration after light irradiation were strained by using Live/Dead® BacLight™ Bacterial Viability Kits and diluted to $1\times10^{-6}$/mL, and 200 μl was divided and added in each well of a 96 well-plate and fluorescence-measured (IVIS-Spectrum), and then a fluorescence amount of survival bacteria was calculated by an ROI value of fluorescence imaging. The image and the evaluation of photo-toxicity for *Propionibacterium acnes* in Example 5 were illustrated in FIGS. 6A and 6B and all of the processes in the Example 5 were performed in a dark room where the light was blocked.

A comparison on effects of a case of using complex particles MBX NPs for phototherapy according to the present invention and a case of using ALA, MAL, and the like as a photosensitive treating agent in the prior arts is illustrated in Table below.

As described in Table below, in the case of treating a skin disease such as acne by using the complex particles for phototherapy according to the present invention, it cannot be seen that a treatment effect is significantly excellent compared with a case of using the ALA, MAL, and the like as a photosensitive treating agent in the prior arts. However, as compared with the treating agent in the prior arts, it is clearly seen that an occlusion time is short and side effects are few, and further, a light protection time for maintaining patient's daily life after treatment is significantly short as compared with ALA, MAL, and the like.

TABLE 1

| Photosensitizer | ALA | MAL | MBX NPs |
| --- | --- | --- | --- |
| Occlusion time after coating | T > 3 hr | T > 3 hr | T = ~10 min |
| wavelength of light source | 417 nm | 630 nm | 633 nm |
| Treatment effect | strong | strong | mild |
| Side effects | Erythema, inflammation, keratin, xeroderma (damage of sebaceous glands) | Erythema, inflammation, keratin, xeroderma (damage of sebaceous glands) | Mild erythema |
| Light protection time after operation | T > 30 hr | T > 30 hr | X (~0 hr) |

The invention claimed is:

1. A methylene blue complex for phototherapy of a skin disease, comprising a methylene blue, a first organic acid, and a second organic acid,
wherein
the complex has a micelle form in which a mixture of the methylene blue and the first organic acid is positioned at a center of the complex and the second organic acid is positioned at an outside of the mixture,
the first organic acid is selected from the group of docosahexaenoic acid (DHA), indole-3-acetic acid (IAA), tranexamic acid, salicylic acid, linoleic acid, linolenic acid, salicylsalicylic acid, acetylsalicylic acid, and methyl salicylic acid,
the second organic acid is oleic acid,
the skin disease is a skin disease caused by *Staphylococcus aureus* or *Propionibacterium acnes*, and
wherein the methylene blue, the first organic acid, and the second organic acid forming the complex micelle have mass ratios of: a mass of the first organic acid is 1 to 5 times greater than the mass of the methylene blue and a mass of the second organic acid is 50 to 500 times greater than the mass of the mixture of the methylene blue and the first organic acid.

2. The methylene blue complex for phototherapy of a skin disease of claim 1, wherein in the phototherapy of the skin disease using the complex, an occlusion time after coating the complex is 1 hour or less, and a light protection time after treatment is 3 hours or less.

3. The methylene blue complex for phototherapy of a skin disease of claim 2, wherein a diameter of the complex is 50 nm or more and 100 μm or less.

4. A composition effective for treating acne caused by acne bacteria or *Staphylococcus aureus*, consisting essentially of a methylene blue complex composed of a methylene blue, a first organic acid, and a second organic acid, wherein the complex has a micelle form in which a mixture of the methylene blue and the first organic acid is positioned at a center of the complex and the second organic acid is positioned at an outside of the mixture,
wherein the first organic acid is selected from the group of docosahexaenoic acid (DHA), indole-3-acetic acid (IAA), tranexamic acid, salicylic acid, linoleic acid, linolenic acid, salicylsalicylic acid, acetylsalicylic acid, and methyl salicylic acid,
the second organic acid is oleic acid, and
wherein the methylene blue, the first organic acid, and the second organic acid forming the complex micelle have mass ratios of: a mass of the first organic acid is 1 to 5 times greater than the mass of the methylene blue and a mass of the second organic acid is 50 to 500 times greater than the mass of the mixture of the methylene blue and the first organic acid.

5. The composition for phototherapy of a skin disease of claim 4, wherein in the phototherapy of the skin disease using the complex, an occlusion time after coating the nanoparticles is 1 hour or less, and a light protection time after treatment is 3 hours or less.

6. The composition for phototherapy of a skin disease of claim 5, wherein a diameter of the complex is 50 nm or more and 100 μm or less.

* * * * *